United States Patent
Grimes

(10) Patent No.: US 6,312,447 B1
(45) Date of Patent: Nov. 6, 2001

(54) DEVICES AND METHODS FOR PERCUTANEOUS MITRAL VALVE REPAIR

(75) Inventor: Randall Y. Grimes, Boston, MA (US)

(73) Assignees: The General Hospital Corporation, Boston, MA (US); The Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 09/417,945

(22) Filed: Oct. 13, 1999

(51) Int. Cl.⁷ .................................................. A61B 17/08
(52) U.S. Cl. ............................................................ 606/219
(58) Field of Search ........................... 606/219, 159, 606/153, 1, 194; 227/175; 623/2; 604/500, 523, 532

(56) References Cited

U.S. PATENT DOCUMENTS

| | | | |
|---|---|---|---|
| 5,423,882 | 6/1995 | Jackman et al. | 607/122 |
| 5,450,860 | 9/1995 | O'Connor | 128/898 |
| 5,478,309 | * 12/1995 | Sweezer et al. | 604/4 |
| 5,522,873 | 6/1996 | Jackman et al. | 607/122 |
| 5,824,065 | 10/1998 | Gross | 623/2 |
| 5,827,237 | 10/1998 | Macoviak et al. | 604/246 |
| 5,833,671 | 11/1998 | Macoviak et al. | 604/247 |
| 5,879,307 | 3/1999 | Chio et al. | 600/485 |
| 5,885,271 | * 2/2000 | Hamilton et al. | 606/1 |
| 6,019,722 | * 2/2000 | Spence et al. | 600/210 |
| 6,165,183 | * 12/2000 | Kuchn et al. | 606/139 |

FOREIGN PATENT DOCUMENTS

| | | | |
|---|---|---|---|
| 11-89937 | 9/1997 | (JP) | A61M/25/00 |
| WO 99/00059 | 1/1999 | (WO) | A61B/17/10 |
| WO 00/03759 | 1/2000 | (WO) | A61M/25/00 |

* cited by examiner

Primary Examiner—Henry J. Recla
Assistant Examiner—(Jackie)Tan-Uyen T. Ho
(74) Attorney, Agent, or Firm—Nutter, McClennen & Fish, LLP

(57) ABSTRACT

Devices and methods are provided for diagnosing and repairing mitral valve defects such as mitral valve regurgitation. According to an exemplary method, mitral valve function is visualized by transesophageal echocardiography. A catheter (10) is inserted along the venous system of the patient through the left and right atria (a, b) into the mitral valve (26). A suction tip (25) grasps the leaflets (28, 30) of the mitral valve (26) to immobilize and juxtapose the leaflets (28, 30) at a point simulating a stitch, and the mitral valve (26) is again observed to confirm that fastening at that point will repair the prolapse or other defect. The mitral valve leaflets (28, 30) are then fastened together via a fastener such as a staple (44) or shape memory rivet (44). The fastener (44) may be inserted by a stapling assembly (40) in the catheter (10), or by a separate stapler (40) that is inserted along an arterial path from the opposite direction and guided along a transcardiac rail to the immobilized point. Upon completion of the repair process, the mitral valve (26) is once again visualized by transesophageal echocardiography to determine whether repair thereof has been effected.

10 Claims, 7 Drawing Sheets

DEVICES AND METHODS FOR PERCUTANEOUS MITRAL VALVE REPAIR

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates generally to cardiac treatment devices and techniques, and in particular, to methods and devices for diagnosis and repair of mitral valve defects such as mitral valve regurgitation.

BACKGROUND OF THE INVENTION

The mitral valve is one of four heart valves that direct blood through the two sides of the heart. The mitral valve itself consists of two leaflets, an anterior leaflet and a posterior leaflet, each of which are passive in that the leaflets open and close in response to pressure placed on the leaflets by the pumping of the heart.

Among the problems that can develop or occur with respect to the mitral valve is mitral valve regurgitation (MR), in which the mitral valve leaflets become unable to close properly, thus causing leakage of the mitral valve. Severe mitral regurgitation is a serious problem which, if left untreated, can adversely affect cardiac function and thus compromise the patient's quality of life and life-span.

Currently, mitral regurgitation is diagnosed by many indicators, and the mechanism of mitral regurgitation can be accurately visualized by transesophageal echocardiography. The most prevalent and widely accepted current technique to correct mitral regurgitation is to repair the mitral valve via open heart surgery while a patient's heart is stopped and the patient is on cardiopulmonary bypass, a highly invasive procedure that has inherent risks.

Nonetheless, this invasive technique for repairing mitral regurgitation is currently favored because it allows for complete visualization of the mitral valve without the accompanying distraction and disruption of a beating heart, and because it is believed to allow for repair of the mitral valve with an unmatched degree of certainty and accuracy. Non-surgical, percutaneous repair of the mitral valve is not currently utilized because of the perceived difficulty of effecting repair of the mitral valve while the heart is not arrested, and because of the limited amount of space in and around the mitral valve in which to route a repair device or devices.

Accordingly, it would be desirable to provide a less invasive yet equally effective procedure for repairing a mitral valve.

It also would be desirable to provide a procedure for diagnostic manipulation of the mitral valve in order to effectuate mitral valve regurgitation repair.

SUMMARY OF THE INVENTION

These and other desirable objects are attained by a catheter system and catheterization procedure of the present invention, wherein a catheter is configured for percutaneous access to the atrium along the venous system of a patient, and for subsequent positioning of the catheter in between the mitral valve leaflets. The tip of the catheter has a structure defining suction or reverse flow directed radially into the catheter on opposite sides thereof. The catheter suction system captures the rapidly moving leaflets of the mitral valve while the heart is non-arrested such that functioning of the heart is uninterrupted and unaffected. The captured mitral valve leaflets are immobilized and juxtaposed to each other in a small region at the suction catheter tip, simulating an Alfieri mitral valve stitch as discussed in the article of Fucci, C. et al. in *European Journal of Cardio-thoracic Surgery*, 9 (1995), pages 621–7 and in the article of Maisano, F. et al. in *European Journal of Cardio-thoracic Surgery*, 13 (1998), pages 240–246. Preferably, simultaneous transesophageal echocardiography (TEE) provides visualization of the catheter tip placement, confirmation of the immobilization of the mitral valve leaflets and determination of the effectiveness of subsequent stitch position on mitral valve leakage. A fastener such a staple or a shape memory rivet is then placed in the juxtaposed immobilized leaflets to effect the repair of the mitral valve. This repair technique should be particularly effective when the mechanism of mitral regurgitation (MR) is mitral valve prolapse or flail of a mitral leaflet.

In one embodiment of the present invention, the catheter includes an extendable guide wire assembly. Once the mitral valve leaflets are captured via suction from the catheter, the guide wire is advanced forward from a distal tip of the catheter into the ventricle and a second percutaneous assembly is advanced via an arterial route to capture the end of the guide wire and to draw the guide wire out from the heart to guide an endovascular stapler. The stapler is then advanced along the guide wire into position at the immobilized leaflets to staple the leaflets together from the opposite side.

In additional embodiments of the present invention, the catheter assembly itself may apply a fastener from the a trial side. This fastener may be a wire rivet having shape memory coils that assume a form to effect permanent fastening. Particular coil configurations may spread their ends, or may shorten a middle portion to draw captured tissue flaps together, or both. In one of these embodiments, a small balloon or diverter body at the tip of the catheter defines lateral suction paths for effectively positioning the captured leaflets and also serves to direct the fastener through the opposed leaflets. The balloon is then deflated such that the flaps are drawn together and the fastener can reassume its memory shape. In another of these embodiments, a helical shape memory coil fastener carried in the catheter tip is ejected such that it winds through the opposed leaflets with its axis parallel to the plane of the junction.

In any of the embodiments of the present invention, a separate lumen or small pressure chamber at the tip may apply a glue or cement between the captured leaflets to further stabilize the junction.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1:
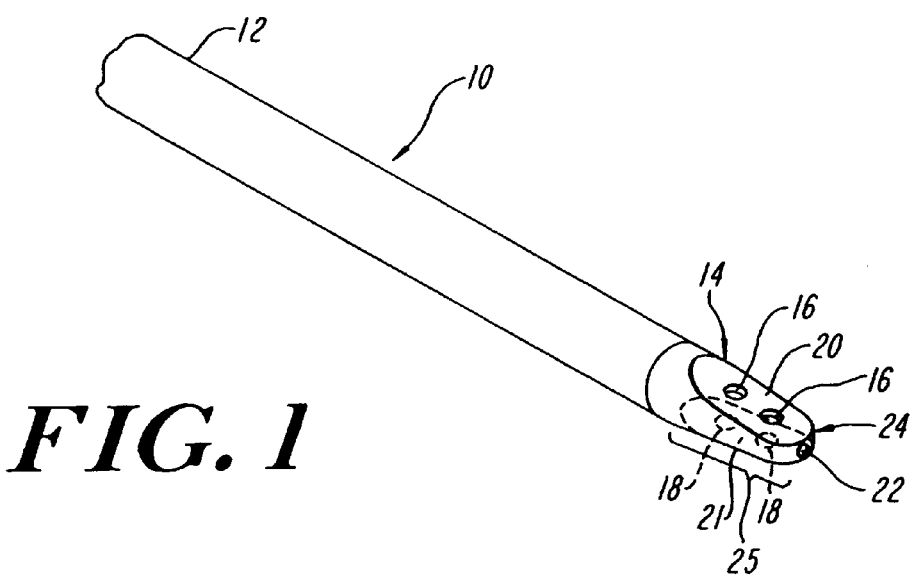
FIG. 1 is a perspective view of a suction catheter in accordance with an embodiment of the present invention.

Referring initially to FIG. 1, a catheter 10 for use with the present invention to repair mitral valve regurgitation is shown. Catheter 10 has a proximal end 12 and a distal end 14 and is sized and shaped as generally known in the art to travel within and along the vascular tree to the heart of a patient. The catheter 10 has at least one opening at or near its distal end 14 in which suction force or reverse flow may be drawn. An exemplary suction catheter 10 has at least one opening 16, 18 respectively on each of the anterior surface 20 and the posterior surface 21 of a suction tip region 25 of the catheter. In a preferred embodiment, the anterior surface 20 and the posterior surface 21 of the tip region 25 of the catheter each have one large opening 16, 18. The tip region 25 of the catheter is depicted in FIG. 1 as being shaped like a duck's bill, which is flattened or tapering, but one of ordinary skill in the art will appreciate that the tip region may have other shapes in accordance with the present invention.

The catheter 10 also contains a guide wire tip opening 22 that is of sufficient size and shape to allow for the insertion of a guide wire (not shown) to position and guide the catheter. In the embodiment shown in FIG. 1, the guide wire opening 22 is at the distal tip 24 of the distal end 14 of the catheter 10, however, one of ordinary skill in the art will appreciate that the position of the guide wire opening 22 may be modified. Furthermore, applicant contemplates that the position(s) and size(s) of one or more of the openings 16, 18 may be varied to effectively operate as described below.

In the practice of the methods of the present invention, this suction tip region, when placed between anterior and posterior leaflets of the mitral valve, is effective to draw the leaflets down flat against its surfaces such that the leaflets are contiguous and immobilized. The catheter enters the mitral annulus from the a trial side.

Figure 2:
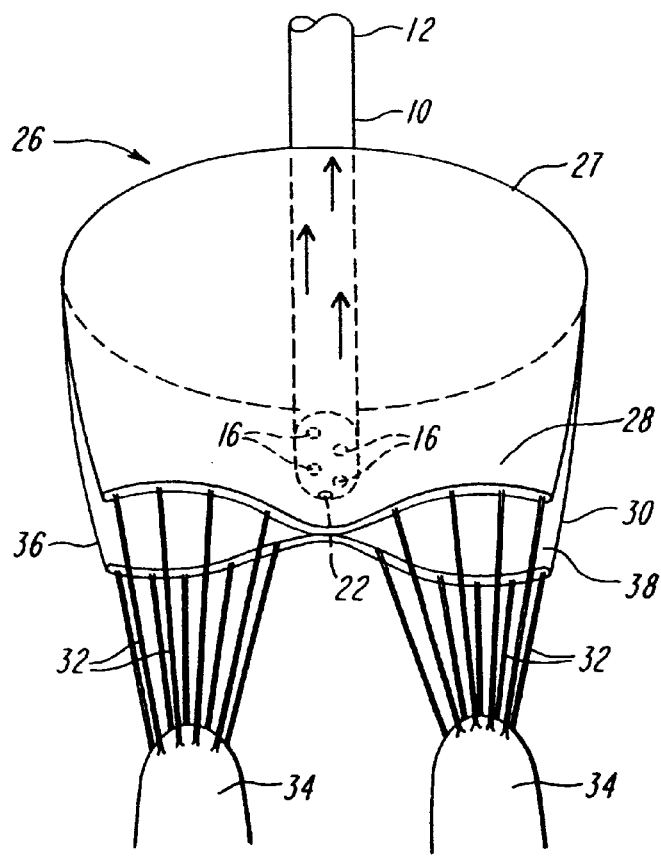
FIG. 2 is a top view of the mitral valve and the suction catheter in accordance with the present invention.

Turning now to FIG. 2, the suction catheter 10 of FIG. 1 is shown having been positioned in proximity of the mitral valve 26. The precise positioning of the catheter 10 is effected by transesophageal echocardiography to place the catheter 10 in, at, or in proximity of the mitral valve 26 such that the catheter may capture the anterior leaflet 28 and posterior leaflet 30 of the mitral valve, while not contacting or harming the fragile chordal tendineae 32 that are attached to the papillary muscles 34. In the embodiment shown in FIG. 2, the catheter 10 has been placed slightly past the mitral annulus 27 and between the leaflets 28, 30; however the catheter may be placed at other locations in, at, or in proximity of the mitral valve 26 while still being able to capture the leaflets 28,30.

The catheter 10 is introduced into a patient's body percutaneously in a modified Seldinger technique via the venous vascular tree through the femoral vein. The catheter 10 then is advanced up the inferior vena cava and into the right atrium of the heart. The catheter 10 then crosses the atrial septum through a small atrial septostomy (created by cardiological techniques known in the art) to enter the left atrium of the heart. For example, a guide wire may be placed across the atrial septostomy and the catheter 10 may then be threaded along the guide wire into the left atrium. The catheter 10 then can be brought to rest at a predetermined locus in, at, or in proximity to the mitral valve 26. For this purpose, the catheter 10 may have a pre-formed or deflectable short hook configuration at its tip region, as discussed further below with regard to FIG. 2A.

As shown in FIG. 2, the catheter 10 applies a suction force or reverse flow from its suction openings 16, 18 in a direction toward its proximal end 12 as indicated by the arrows within the catheter to create a force normal to the surface of the leaflets 28, 30 down against the flat surface of the tip region. This suction force is of a magnitude that is effective to capture the leaflets 28, 30 of the mitral valve 26. The capturing of the leaflets 28, 30 is preferably confirmed via transesophageal echocardiography. If the suction has not captured the leaflets 28, 30, the suction may be stopped, the tip region re-positioned against a first one of the leaflets, then the other one of the leaflets, and then the suction may be reapplied until such time as transesophageal echocardiography can confirm that the leaflets have been properly captured. In the FIG. 2 embodiment, the suction force has caused both the anterior leaflet 28 and posterior leaflet 30 to adhere to the catheter 10 about midway between their edges, thus creating a double orifice 36, 38 mitral valve 26. Data set forth in the above-cited article of Maisano, F. et al. in *European Journal of Cardio-thoracic Surgery*, 13 (1998), pages 240–246 confirms that this double orifice mitral valve neither creates an impediment to ventricular filling, nor causes a significant pressure gradient across the mitral valve 26.

The positioning of the catheter 10 and the capturing of the mitral valve 26 leaflets 28, 30 as described above can be advantageously performed percutaneously without disrupting the normal functioning of the mitral valve (i.e., the valve continues to open and close as the heart pumps) since the non-captured portions of the leaflets continue to move in response to flow. Also, by introducing the catheter 10 via the atrium, one avoids associated problems that would occur with a ventricular approach to the valve 26. For example, due to the anatomy of the mitral valve system, entry through the ventricle would only allow movement of the catheter to access to the mitral valve leaflets 28, 30 along a central path directly between the leaflets, thus potentially limiting the ability of the catheter 10 to effectively capture the leaflets, or to repair prolapse or flail located close to a commisure. The present invention, by approaching the mitral valve 26 via the atrium, allows for positioning of the catheter at nearly any edge or central location of the mitral leaflets by virtue of the catheter 10 being free to maneuver at any position in the annulus of the mitral valve and to come to rest within the valve or at either of the valve commisures. If necessary, the dimensions of the catheter 10 may be altered to more readily allow for particular positioning and/or maneuvering of the catheter.

Figure 2A:
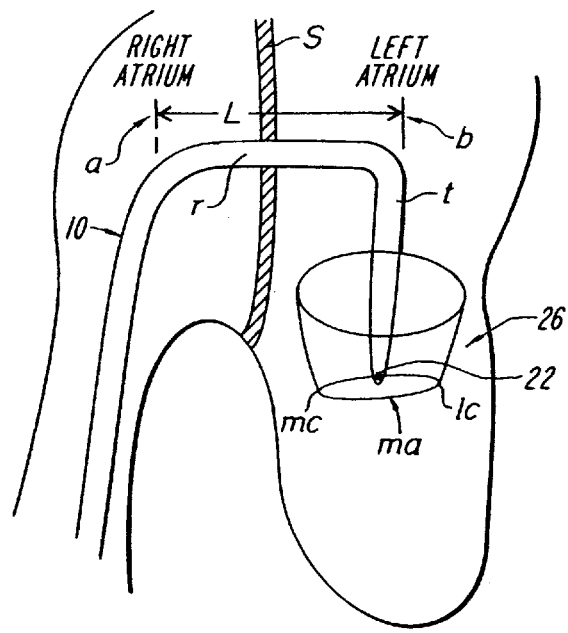
FIG. 2A is a schematic view in vertical section of the suction catheter positioned in the heart.

FIG. 2A shows a schematic vertical section through the heart, wherein a further embodiment of the suction catheter 10 is positioned at the mitral valve 26. In this embodiment, the catheter 10 has a distal region characterized by a preformed U-turn with a base segment r of length L that defines a precise reach of the catheter tip 25 past the atrial septum to position the distal tip length t within the mitral valve opening. The length L between corners a, b of the reach segment r places the suction gripping nozzle 22 at the medial commisure mc, the lateral commisure lc, or centrally in the mitral annulus region ma. The predetermined contour with reach L may be implemented by forming the distal end of the catheter with a catheter tube having sufficient stiffness to hold a pre-formed U-configuration, in which case a straightener may be inserted when initially placing the catheter 10, and withdrawn as the catheter tip passes the septum S. Alternatively, various steering wire arrangements may be employed wherein one or more tension wires pass within the catheter interior are operated to form one or more bends that position the suction tip at the desired spot in the mitral valve 26.

In accordance with a further aspect of the invention, once the leaflets have been captured and the effectiveness of an intended suture point has been verified to cure the prolapse or other defect, the immobilized leaflets are permanently fastened at the identified site. This is preferably accomplished using a percutaneously-inserted stapling device, which may, in different embodiments, be incorporated in the tip assembly, or may be guided to the immobilized site along a rail or guide wire.

Figure 3:
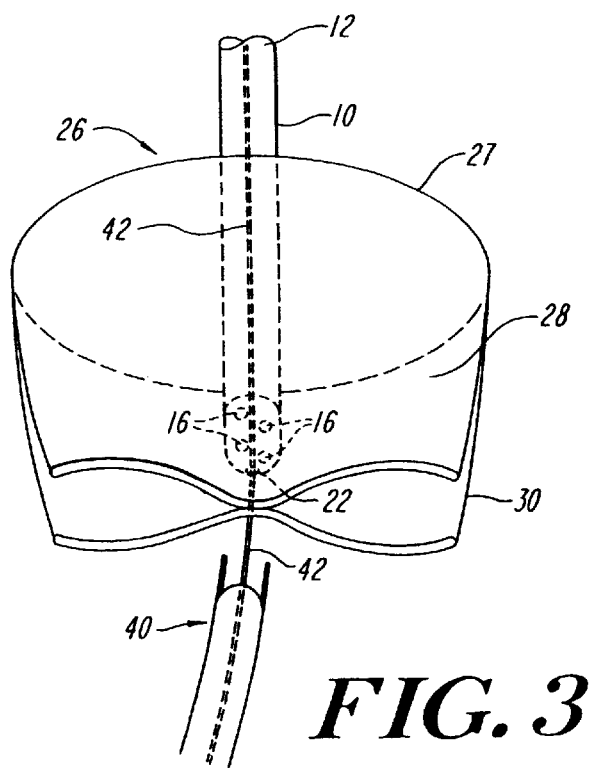
FIG. 3 is a top view of the mitral valve, the suction catheter and a stapling device in accordance with the present invention.

Referring now to FIG. 3, a stapling device 40 is shown in addition to the mitral valve 26 and catheter 10 of FIG. 2. The catheter 10 has captured the anterior and posterior leaflets 28, 30 of the mitral valve 26 as described above with respect to FIG. 2. A flexible J-tipped guide wire 42 is then advanced through the suction catheter 10 and out of the guide wire opening 22, and the guide wire 42 is captured by another percutaneous device and drawn out of the heart via the aortic valve. The guide wire 42 then continues to the femoral artery, and is pulled into a vascular sheath. The stapling device 40 is introduced into the femoral artery along the guide wire 42, and using the guide wire 42 as a rail, the stapling device is guided to the mitral valve 26 following the reverse path so that the jaws of the stapling device are positioned exactly at the immobilized site. This guide wire procedure allows the stapling device 40 to follow a smooth path to the leaflets 28, 30, without lateral movements that could damage the delicate web of chordae arranged in the left ventricle and extending from the leaflets.

Figure 4:
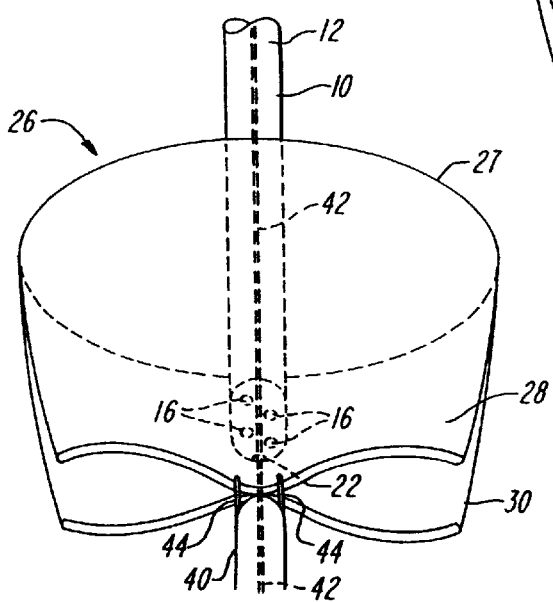
FIG. 4 is a top view of the mitral valve during the stapling process.
Figure 5:
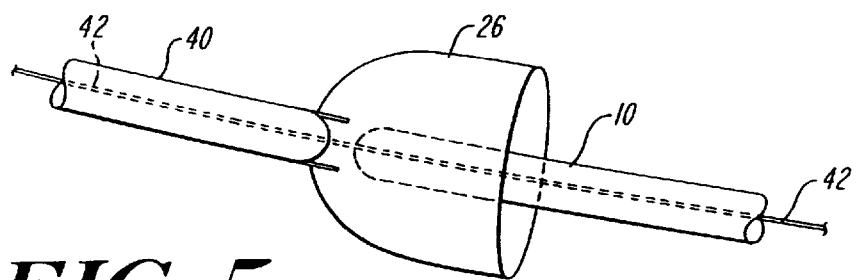
FIG. 5 is a side view of the mitral valve during the stapling process.

Referring now to FIG. 4, the stapling device 40 has been advanced via the guide wire 42 to a position wherein it may deliver one or more pins 44 (two pins are shown in FIG. 4) across the mitral valve anterior and posterior leaflets 28, 30. FIG. 5 also shows the mitral valve 26, the suction catheter 10 and the stapling device 40 in preparation for the delivery of the staple pins to the leaflets by the stapling catheter.

Figure 6:
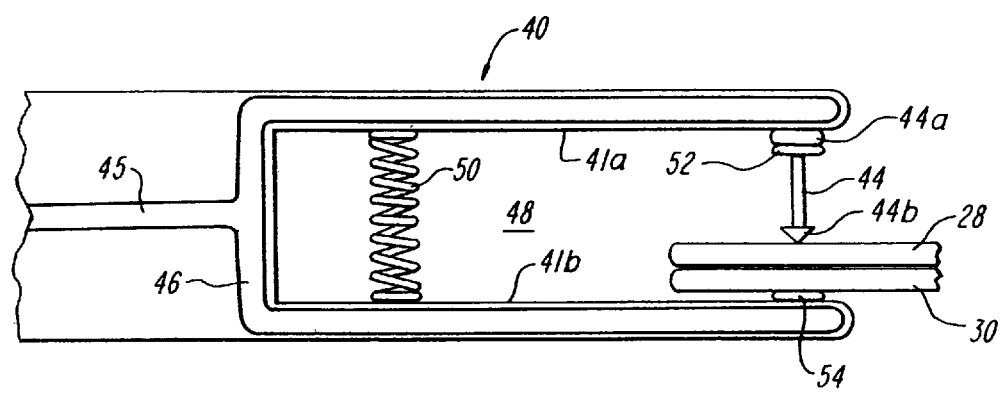
FIG. 6 is a side view, with partial cut away, of the stapling catheter of FIGS. 3–5 during the stapling process.

FIG. 6 shows an enlarged view of one embodiment of such a stapling device 40 just before delivery of a pin 44 to the anterior and posterior leaflets 28, 30. In this embodiment, the pin or staple 44 is a tack-shaped rivet, having a head 44a and a spreadable point 44b. The force required to staple the pin 44 across the leaflets 28, 30 is generated by inflation, via a fluid inflation line 45, of a balloon 46 that bears against an inner chamber 48 or wall of the jaws 41a, 41b of the stapling device 40.

Because of the path it follows to the mitral valve 26 (noted above with respect to FIG. 3), the stapling device 40 is preferably implemented with curved flexible tubes, preferably using a liquid or substantially incompressible fluid, to deliver the motive force to the distal tip. These tubes also allow for fluid to be delivered to inflate the balloon 46 to provide the force to deliver one or more pins 44 to the leaflets 28, 30 without stiffening the catheter wall or interfering with the catheter contour or deflection of the tip.

Once the leaflets 28, 30 are immobilized in the proper location to be stapled (again confirmed by transesophageal echocardiography), the balloon 46 is inflated via the fluid inflation line 45. The inflation of the balloon 46 presses both walls of the inner chamber 48 and both jaws 41a, 41b of the stapling device 40 inwardly, and spring 50 located within the inner chamber. The inflation of the balloon 46 forces the pin 44 through the leaflets 28, 30, and spreads the point 44b of the pin, thus riveting the leaflets together. Following the delivery of the pin 44, the balloon 46 is deflated and the spring 50 recoils, thus freeing the stapled leaflets from the stapling device 40. Another mechanism to effect recoil of the stapling device is an additional balloon (not shown) in lieu of the spring 50. The additional balloon, when inflated, causes the jaws 41a, 41b of the stapling device 40 to separate. Following the delivery of the pin 44, the stapling device 40 may be removed from the mitral valve area by reversing its path of insertion.

One of ordinary skill in the art will readily appreciate that the balloon 46 is not necessarily needed in order to deliver the pin 44 across the leaflets 28, 30 and that other motive assemblies commonly used in stapler mechanisms may be adapted to the illustrated access geometry. One of ordinary skill in the art will also appreciate that more than one pin 44 may be deployed (see, e.g., FIGS. 4 and 8), and also that one or all of the one or more pins 44 may have a different configuration than that which is described above.

Figure 7:
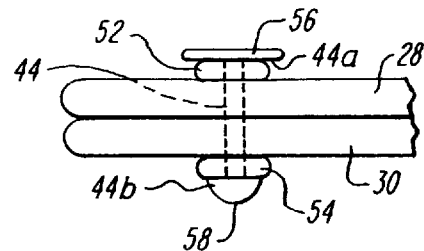
FIG. 7 is a side view of the mitral valve leaflets following the stapling process.
Figure 8:
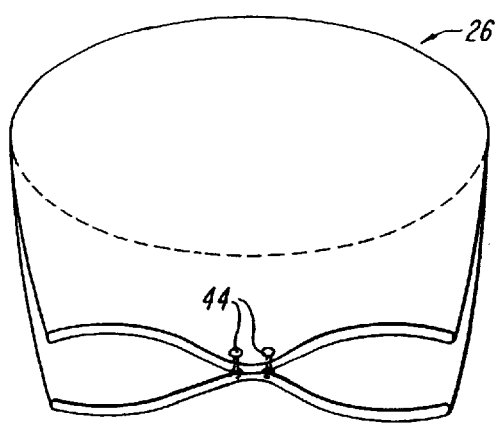
FIG. 8 is a top view of the mitral valve following the stapling process.

The embodiment of FIG. 6 may optionally employ anterior and posterior padding elements 52, 54. The padding elements 52, 54 may be provided such that the one or more pin 44, once deployed, does not rest directly against the fragile mitral valve 26 leaflets 28, 30 (see FIG. 7), and such that the point 44b of the pin 44 is captured and secured by a precisely preconfigured opening in the posterior padding element. In a preferred embodiment, the anterior padding element 52 is positioned between a first end 56 of the pin 44 and the anterior leaflet 28, while the posterior padding element 54 is positioned between a second end 58 of the pin and the posterior leaflet 30. The padding elements 52, 54 may also have adhesive properties that help secure the pin or pins 44 to the mitral valve. FIG. 8 depicts the mitral valve following deployment of two pins 44 and subsequent removal of the suction catheter 10 via the reversal of the path by which it was inserted as described above.

In addition to a transcardiac guide wire procedure wherein the immobilized mitral valve leaflets are percutaneously fastened by a stapling device deployed along the arterial tree, the present invention also contemplates a procedure and device for effecting such repair entirely from the atrial side. In that case, the necessary fastening assembly is incorporated in the tip of the leaflet-grabbing catheter.

Figure 9:
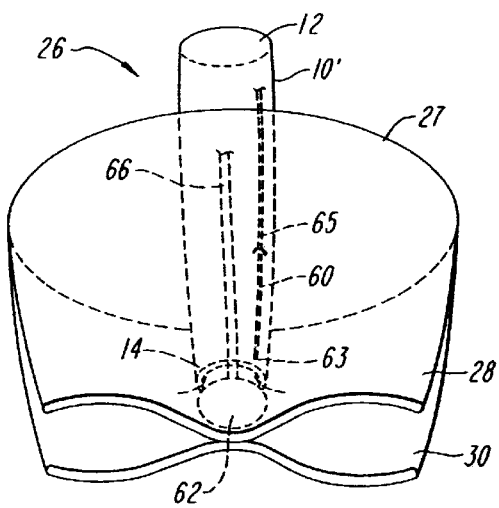
FIG. 9 is a top view of a shape memory fastener deployment system of the present invention.

Turning now to FIG. 9, such an additional embodiment of a catheter 10' is shown in which mitral regurgitation repair is effected using a shape memory fastener 60. In this embodiment, a suction catheter 10' is placed at or near the mitral valve 26 as described above with respect to the FIGS. 1–8 embodiment. The suction catheter 10' also captures the anterior and posterior leaflets 28, 30 of the mitral valve as described above. Placement of the catheter and capture of the leaflets 28, 30 are again confirmed and visualized by transesophageal echocardiography.

Figure 10:
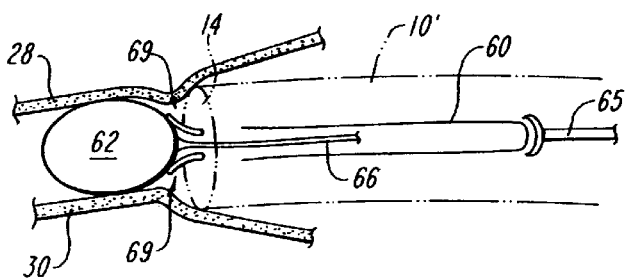
FIG. 10 is a side view, with partial cut away, of the catheter of FIG. 9

The suction catheter 10' of FIG. 9 differs from the catheter described in the FIGS. 1–8 embodiment in several respects. First, the catheter 10' does not contain suction ports in opposed flat faces in order to effectuate suction, but rather contains an obstruction balloon 62 at its distal end 14, the balloon having a trailing fluid inflation line 66 to effect inflation and deflation thereof and being placed so that it defines lateral suction draw paths 69 (see FIG. 10) into the tip region of the distal end of the catheter. As shown in FIG. 9, the balloon 62 may be placed between the leaflets 28, 30 such that the flaps are drawn together in the suction region.

Figure 11:
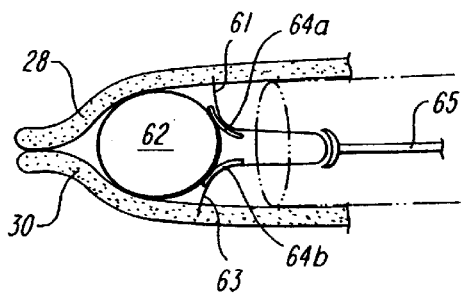
FIG. 11 is a side view, with partial cut away, of the catheter of FIGS. 9–10 during deployment of the shape memory fastener.
Figure 12:
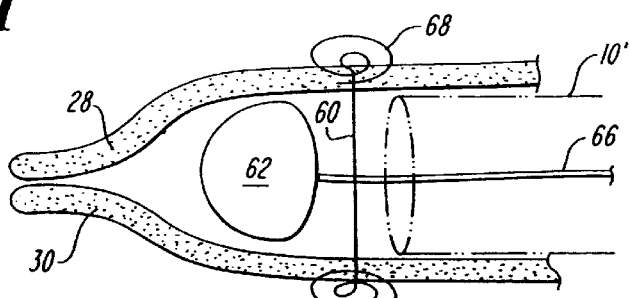
FIG. 12 is a side view, with partial cut away, of the catheter of FIGS. 9–10 following deployment of the shape memory fastener.

The catheter 10' has a tip assembly configured to contain a fastener 60 of shape memory material. While inside the catheter 10', the fastener 60 is uncoiled (see FIG. 9). The shape memory fastener 60 may be moved within the catheter 10' by a placement device 65, such as a plunger (see FIGS. 10–11) or telescopic cylinder. The plunger 65 is configured to push the shape memory fastener 60 toward the distal end 14 of the catheter 10'. The shape memory fastener 60 is then distally guided out of the distal end 14 of the catheter 10' and its ends 61, 63 are deflected outwardly, and forced to curve, by the shape of a pair of guiding channels 64a, 64b at the rear face of the balloon 62 so that the fastener penetrates the opposed anterior and posterior leaflets 28, 30. Specifically, a first end 61 of the shape memory fastener 60 is inserted into the anterior leaflet 28, and a second end 63 of the shape memory fastener is inserted into the posterior leaflet 30. Continued pushing of the plunger 65 in a distal direction drives the shape memory fastener 60 further through the leaflets 28, 30, and the first end 61 of the shape memory fastener 60 forms an anterior coil 68, while the second end 63 of the shape memory fastener forms a posterior coil 70, while the remainder of the shape memory fastener straightens as shown in FIG. 12 due to the presence of the balloon 62, which separates the leaflets.

Figure 13:
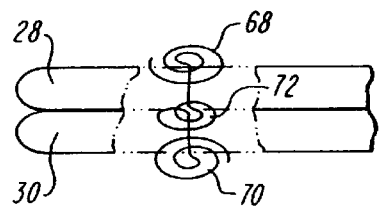
FIG. 13 is a side view of the mitral valve leaflets following the deployment of the shape memory fastener of FIGS. 9–12.
Figure 14:
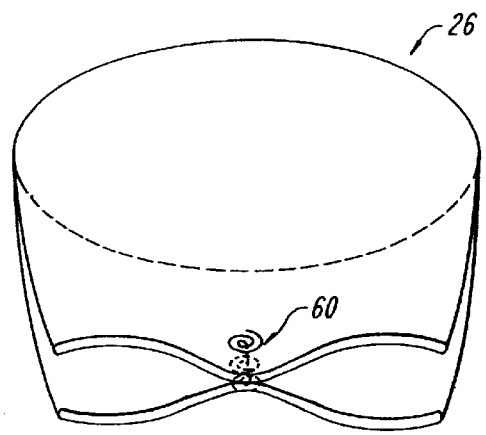
FIG. 14 is a top view of the mitral valve following deployment of the shape memory fastener of FIGS. 9–12.

Once the shape memory material 60 has secured the leaflets 28, 30, as verified by transesophageal echocardiography, the balloon 62 is deflated and the catheter 10' is removed. Following deflation of the balloon 62 and removal of the catheter 10', the central portion of the fastener 60 reassumes a shape and forms a third coil 72 between the anterior coil 68 and the posterior coil 70 as shown in FIG. 13. The formation of this third coil is not necessarily required and one of ordinary skill in the art will appreciate that the fastener may also form more than three coils. The coils 68, 70, 72 draw the two flaps together, effectively riveting or suturing the valve closed at the site of the defect. The mitral valve 26 is shown in FIG. 14 following the removal of the balloon 62 and catheter 10'.

The shape memory fastener as described above with respect to the embodiment depicted in FIGS. 9–14 is generally in the form of a rivet or other shape conducive to being contained within a catheter, and to being installed with a simple ejection mechanism such as a plunger. The illustrated shape memory fastener 60 includes at least two coils (the anterior coil and the posterior coil), and may form greater than three coils. Exemplary shape memory materials include, but are not limited to, superelastic materials such as super elastic nickel titanium and stainless steel, and certain phase change thermal memory materials. The illustrated fastener employs spiral coils, each lying in a plane perpendicular to the nominal axis of the fastener to provide a broad seating surface for each end of the fastener and a tightening retraction or shortening of the fastener length. However, other forms of fastener devices, including staples and shape memory fasteners of known configuration, may also be adapted for catheter delivery at a suction tip for the practice of the invention. Thus, for example, a single helical shape memory coil fastener may be carried in the catheter tip and ejected so as to wind through the opposed leaflets with its axis parallel to the plane of the junction. Furthermore, an additional lumen or ejection assembly may be configured to eject a dollop of a compatible bioadhesive at the stapling site to enhance the fastening.

In addition to the embodiment described above with respect to FIGS. 9–14 in which the shape memory fastener 60 is deployed by a plunger placement device 65, the shape memory fastener 60 may be deployed using other placement devices as shown in FIGS. 15–23 and as described below.

Figure 15:
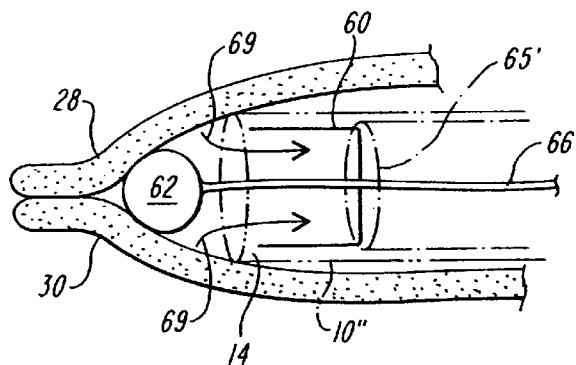
FIG. 15 is a side view, with partial cut away, of an alternate embodiment of the shape memory fastener deployment system of FIGS. 9–14.

Referring now to FIG. 15, a system for deployment of a shape memory fastener 60 is shown. This system, like the system described above with respect to FIGS. 9–14, utilizes a partial obstruction balloon 62 to define suction flows so as to capture the mitral valve leaflets 28, 30. The balloon 62 is inflated via a trailing fluid inflation line 66 such that suction paths 69 are defined and the leaflets 28, 30 are drawn together as confirmed by transesophageal echocardiography . The balloon 62 is then deflated and withdrawn, which causes the leaflets 28, 30 to collapse around the shape of a catheter 10".

A shape memory fastener 60 is contained within the catheter 10" as is a placement device 65'. Following deflation of the balloon 62, the fastener 60 is captured by the placement device 65' and is moved within the catheter 10" toward the distal end 14 of the catheter by distal pushing of the placement device within the catheter. In this embodiment, the placement device 65' is a telescoping cylinder but placement devices of other shapes such as a plunger blade may alternatively be used as long as the placement device is sized and shaped so as to be able to move within the catheter while still being able to capture and cause distal movement of the fastener.

Figure 16:
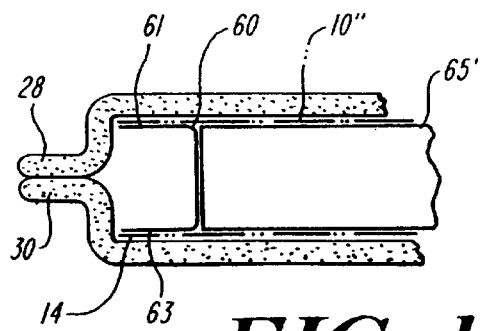
FIGS. 16–17 are side views, each with partial cut away, of the system of FIG. 15 during two stages of the deployment of a shape memory fastener.
Figure 17:
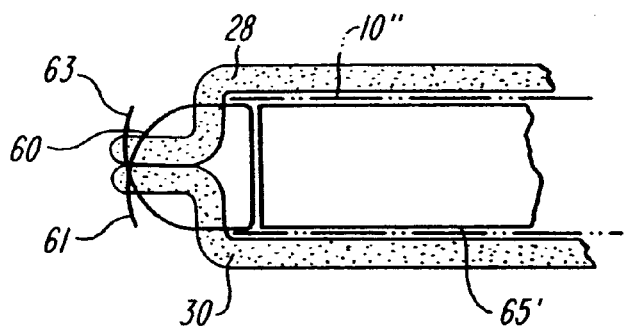

As shown in FIG. 16, the distal pushing of the placement device 65' within the catheter 10" causes the fastener 60 to move to the distal end 14 of the catheter (at which the leaflets 28, 30 have been captured as described above) such that the first and second ends 61, 63 of the fastener 60 approach the leaflets 28, 30. Continued distal pushing of the placement device 65' within the catheter 10" eventually causes the insertion of the first end 61 of the fastener 60 into the anterior mitral valve leaflet 28, and the second end 63 of the fastener into the posterior mitral valve leaflet 30. As shown in FIG. 17, further pushing of the placement device 65' within the catheter 10" causes the inserted ends 61, 63 of the fastener 60 to coil over such that each end also proceeds to penetrate and wind through the other leaflet. As before, these fasteners 60 may be formed of a superelastic or shape memory material, and the ejection of the fastener is performed slowly to allow the coil shape to wind through and suture together the two captured tissue regions.

Figure 18:
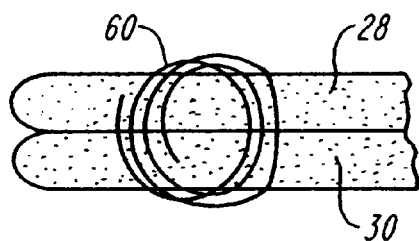
FIG. 18 is a side view of the mitral valve leaflets following deployment of the shape memory fastener of FIGS. 15–17.
Figure 19:
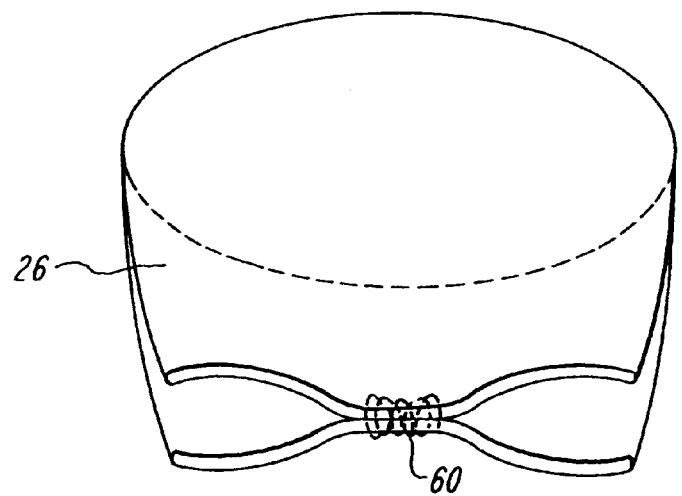
FIG. 19 is a top view of the mitral valve following deployment of the shape memory fastener of FIGS. 15–18.

The distal pushing of the placement device 65' within the catheter 10" is completed when the placement device reaches the distal end 14 of the catheter or when the coiling of the fastener with respect to the leaflets 28, 30 has assured the closing of the valve at the site of the valve defect as verified by transesophageal echocardiography, at which time the catheter and the placement device can be withdrawn. FIGS. 18 and 19 show the mitral valve leaflets 28, 30 (FIG. 18) and the mitral valve 26 (FIG. 19) in a vertical section along the AP plane, and a front plan view, respectively, with the fastener 60 having formed three coils therewithin. The number of coils that the fastener 60 may form within the leaflets 28, 30 can be greater or less than three subject to the constraint that the wire must exert adequate holding force against the mitral valve tissue. During installation, assurance is provided via transesophageal echocardiography that the valve is properly closed at the site of the valve defect.

Another alternate shape memory deployment system is shown in FIGS. 20–23. This embodiment, like the systems described above with respect to FIGS. 9–14 and 15–19, utilizes a partial obstruction balloon in order to effectuate suction to capture the mitral valve leaflets 28, 30. The balloon is inflated via a trailing fluid inflation line such that suction paths 69 are defined and the leaflets 28, 30 are drawn together. The effectiveness of the intended suture site may be confirmed by transesophageal echocardiography. The balloon is then deflated, so that the leaflets 28, 30 collapse around and conform against the shape of a catheter 10'''.

In this embodiment, however, instead of the fastener 60 being maneuvered via a plunger placement device (see FIGS. 9–14) or a distally-pushed placement device as shown and described with respect to FIGS. 15–19, the shape memory fastener 60 is threaded into the leaflets 28, 30 via the concurrent distal pushing and rotation of a placement device 65". In this embodiment, the placement device is a telescoping cylinder but other placement devices may alternatively be used as long as the placement device is sized and shaped so as to be able to move within the catheter while still being able to capture and cause distal movement of the fastener.

Figure 20:
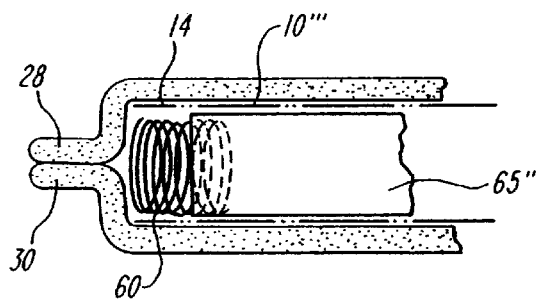
FIG. 20 is a side view, with partial cut away, of another alternate embodiment of the shape memory fastener deployment system of the present invention.
Figure 21:
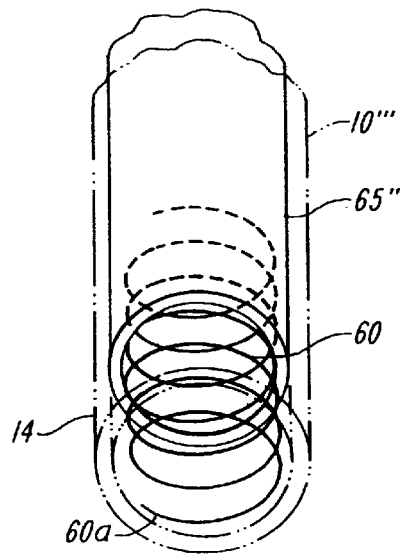
FIG. 21 is a top perspective view of the system of FIG. 20 during deployment of a shape memory fastener.
Figure 22:
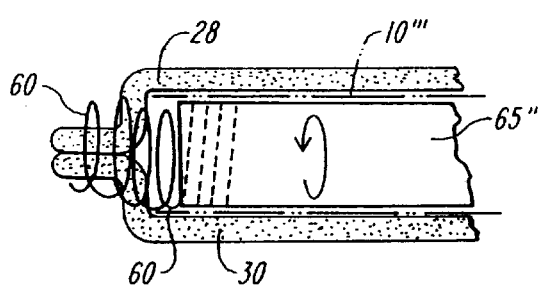
FIG. 22 is a side view, with partial cut away, of the system of FIG. 20 during deployment of a shape memory fastener.

Referring now to FIGS. 20–21, a placement device 65" is contained within a catheter 10'''. A shape memory fastener 60 has been partially threaded into the wall of the placement device 65"such that the placement device can still freely move within the catheter 10''', and also such that a predetermined portion 60a, illustrating a penetrating free end, of the fastener is not threaded into the placement device. This predetermined portion 60a of the fastener 60 should be long enough to assure that it can be inserted and advanced into, and maintained within a mitral valve leaflet 28, 30. It may be, for example, captured and deflected in a generally forward direction by a guide groove in the interior wall of the catheter 10''', or may simply project sufficiently forward to penetrate the adjacent captured valve tissue.

The placement device 65"is moved toward the distal end 14 of the catheter 10''' where the leaflets 28, 30 have been captured as described above and is simultaneously rotated. With continued distal movement and rotation of the placement device 65" within the catheter 10''', the predetermined portion 60a of the fastener 60 penetrates either the anterior or posterior leaflet 28, 30 as can be confirmed by transesophageal echocardiography and continues to wind through both leaflets, forming a multi-turn coil, thus binding together the leaflets 28, 30 as shown in exemplary FIG. 22.

Figure 23:
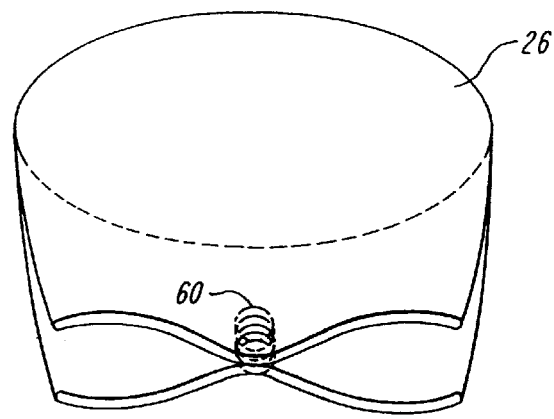
FIG. 23 is a top view of a mitral valve following deployment of the shape memory fastener of FIGS. 20–23.

The distal pushing and rotation of the placement device 65" within the catheter 10''' is completed (at which time the catheters can be withdrawn) when the placement device reaches the distal end 14 of the catheter, and when the coiling of the fastener with respect to the leaflets 28, 30 has assured the closing of the valve at the site of the valve defect as verified by transesophageal echocardiography. FIG. 23 is a front plan view of the mitral valve similar to that of FIG. 19 showing the disposition of this fastener 60 having formed three coils therewithin. The number of coils that the fastener 60 may form within the leaflets 28, 30 can be greater or less than three subject to mechanical design constraints and the mechanics of the valve tissue. During installation, adequate assurance is provided via transesophageal echocardiography that the valve is properly closed at the site of the valve defect, and removal of that the catheter and placement device will not cause the coils to be withdrawn from the leaflets.

The shape memory fastener 60 as described above with respect to the embodiments depicted in FIGS. 9–23 is generally in the form of a rivet, staple, wire suture or other shape conducive to being contained within a catheter, and to being installed with a simple placement device such those described above. Exemplary shape memory materials include, but are not limited to, superelastic materials such as super elastic nickel titanium alloy and stainless steel, and certain phase change thermal memory materials or shape memory alloys.

Additionally, in lieu of or in conjunction with any of the above-described embodiments, other methods and devices may be used to assure the proper repair of captured mitral valve leaflets. For example, a cardiac glue, such as that known in the art as Cardia, may be applied to hold the mitral valve leaflets together. Also, cauterization may be used in order to hold the mitral valve leaflets together. Preferably, cardiac glue or cauterization, if used, are applied in addition to the solid fastening element as described above.

One skilled in the art will appreciate further features and advantages of the invention based on the above-described embodiments. Accordingly, the invention is not to be limited by what has been particularly shown and described, but is defined by the claims appended hereto and equivalents thereof. All publications and references cited herein are expressly incorporated herein by reference in their entirety.

What is claimed is:

1. An endovascular system for cardiac treatment, such system comprising:
   a first elongated catheter body adapted for percutaneous insertion along the venous system of a patient to the patient's heart, said catheter body including means for accommodating a guide wire;

means for advancing a guide wire through said catheter body and along the arterial tree of the patient;

a suction assembly disposed at a distal end of said catheter body, the suction assembly being effective to define negative flow into said catheter body along opposed sides thereof, whereby insertion of the catheter into the atrium with the distal end of the catheter positioned in the mitral valve is effective to draw opposed leaflets of said mitral valve together in juxtaposition for simulating an Alfieri leaflet stitch repair; and a second, separate securing device adapted for percutaneous insertion and for travel along said guide wire such that the securing device may be positioned to secure to each other the opposed leaflets drawn together by the distal end of the catheter assembly.

2. The device of claim 1, wherein the securing device includes an inflation element which, when in a substantially inflated state, is effective to cause the securing device to deploy a securing element to secure the opposed leaflets together.

3. The device of claim 2, wherein the inflation element is a balloon.

4. The device of claim 2, wherein the inflation element is inflated via fluid delivery from a fluid source.

5. The device of claim 4, wherein the fluid source is located external to the catheter body.

6. The device of claim 2, wherein the securing element is selected from the group consisting of at least one pin, at least one staple, at least one fastener and at least one rivet.

7. The device of claim 6, wherein each of the at least one fasteners is made of a shape memory material.

8. The device of claim 6, wherein the rivet has a first substantially flat end and a second substantially pointed end.

9. The device of claim 2, wherein the securing element has a first end and a second end, and wherein, once deployed, the first end is in communication with an anterior one of the opposed leaflets, and the second end is in communication with a posterior one of the opposed leaflets.

10. The device of claim 9, wherein a first padding element is disposed between the first end of the securing element and the anterior leaflet and a second padding element is disposed between the second end of the securing element and the posterior leaflet.

* * * * *